United States Patent
Hart et al.

(10) Patent No.: US 7,438,702 B2
(45) Date of Patent: Oct. 21, 2008

(54) MULTI-SEAL TROCAR SYSTEM

(75) Inventors: Charles C. Hart, Summerville, SC (US); John R. Brustad, Dana Point, CA (US); Nabil Hilal, Laguna Niguel, CA (US); Said S. Hilal, Coto de Caza, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 819 days.

(21) Appl. No.: 10/495,671

(22) PCT Filed: Nov. 13, 2001

(86) PCT No.: PCT/US01/45567

§ 371 (c)(1),
(2), (4) Date: May 13, 2004

(87) PCT Pub. No.: WO03/043683

PCT Pub. Date: May 30, 2003

(65) Prior Publication Data

US 2005/0033342 A1     Feb. 10, 2005

(51) Int. Cl.
*A61M 5/178* (2006.01)
*A61B 17/34* (2006.01)

(52) U.S. Cl. ............... 604/167.03; 604/167.01; 604/164.01; 606/185

(58) Field of Classification Search ......... 604/167.01–167.06; 606/108, 191, 184, 185
See application file for complete search history.

(56) References Cited

U.S. PATENT DOCUMENTS

| | | |
|---|---|---|
| 5,104,383 A | 4/1992 | Shichman |
| 5,197,955 A | 3/1993 | Stephens |
| 5,209,737 A | 5/1993 | Ritchart |
| 5,308,336 A | 5/1994 | Hart |
| 5,385,553 A | 1/1995 | Hart |
| 5,407,433 A | 4/1995 | Loomas |
| 5,411,483 A | 5/1995 | Loomas |

(Continued)

FOREIGN PATENT DOCUMENTS

DE     297 17 940 U1     11/1997

(Continued)

OTHER PUBLICATIONS

European Patent Office, Supplementary Partial European Search Report for PCT application No. PCT/US01/45567.

*Primary Examiner*—Julian W Woo
(74) *Attorney, Agent, or Firm*—Kenneth K. Vu; Patrick Y. Ikehara; Pui Tong Ho

(57) ABSTRACT

A multi-seal trocar system (10) includes a plurality of co-axial sealing elements (30 60,80) adapted for forming a seal with either a large or small instrument. Small and large scaling elements (45,62) are disposed in an in-line arrangement such that a single port is provided for instrument insertion. A zero seal (80) is disposed distally of the sealing elements to seal a working channel of the system and to prevent backflow when no instruments are inserted The small sealing element (45) is configured such that insertion of a large instrument automatically moves the small sealing element (45) out of its path, thereby avoiding contact with the large instrument.

8 Claims, 14 Drawing Sheets

U.S. PATENT DOCUMENTS

| | | |
|---|---|---|
| 5,476,475 A | 12/1995 | Gadberry |
| 5,531,758 A | 7/1996 | Uschold |
| 5,545,142 A | 8/1996 | Stephens |
| 5,554,124 A | 9/1996 | Alvarado |
| 5,569,205 A | 10/1996 | Hart |
| 5,603,702 A | 2/1997 | Smith |
| 5,628,732 A | 5/1997 | Antoon |
| 5,634,908 A | 6/1997 | Loomas |
| 5,792,113 A | 8/1998 | Kramer |
| 5,820,600 A * | 10/1998 | Carlson et al. ......... 604/167.03 |
| 5,827,228 A | 10/1998 | Rowe |
| 6,228,061 B1 | 5/2001 | Flatland |
| 6,923,783 B2 * | 8/2005 | Pasqualucci ........... 604/167.01 |

FOREIGN PATENT DOCUMENTS

| | | |
|---|---|---|
| EP | 0 696 459 A1 | 2/1996 |
| WO | WO 98/53865 | 12/1998 |

* cited by examiner

MULTI-SEAL TROCAR SYSTEM

This application is a 371 of PCT/US01/45567, filed Nov. 13, 2001.

BACKGROUND OF THE INVENTION

1. Field of the Invention

The present invention relates generally to medical and surgical devices, and more specifically to trocar assemblies.

2. Description of Prior Art and Related Information

Trocar assemblies, or simply trocars, are generally used in minimally invasive surgeries such as laparoscopy. Such procedures require that any instrumentation inserted through a trocar assembly into the body be sealed in order to prevent gases from entering or exiting the body, such as in the case of a laparoscopic surgery where the accessed abdominal cavity has been insufflated.

The need to provide a tight seal is countered by several other demands, including the need to accommodate instruments of varying sizes as well as the need to allow for movement of the instrument within the trocar assembly. In an effort to fulfill these competing requirements, attempts have been made to provide a universal seal composed of a single material with a single orifice that can be adjusted to accommodate instruments of different sizes.

A material that works well for a small instrument, however, might not be suitable for a large instrument. Attempting to accommodate both a small instrument and a large instrument with a single seal is especially difficult given the fact that a small instrument has a greater range of lateral, or side-to-side, movement than a large instrument. If the material is too compliant, the seal will leak with a small instrument due to the wide range of lateral movement. If the material is less compliant, the force required to dilate the seal in order to accommodate large instruments may be too great. Such a dilemma is only one of several involved attempting to provide a single, universal seal in a trocar.

Even if a single universal seal could be dilated in order to accommodate both large and small instruments, trocars which must be dilated present another obvious problem. In a typical laparoscopic surgery, a "free hand" is seldom available to manually adjust the trocar. Yet, several attempts have been made to provide adjusting mechanisms which would require manual manipulation.

Thus, the varying diameters of different sized instruments, the varying side-to-side motion of different instruments, and the lack of a free hand for manual adjustment all contribute to the difficulty of providing an effective and convenient trocar.

SUMMARY OF THE INVENTION

The present invention provides structures and methods which overcome the deficiencies of the prior art.

In one aspect, a trocar system is provided for alternatively forming a first seal with a small instrument having a first diameter and a second seal with a large instrument having a second diameter larger than the first diameter. The system comprises a first seal assembly, a second seal assembly, and a third seal assembly, all of which are preferably arranged in a coaxial relationship. Configured to form the first seal with the small instrument, the first seal assembly comprises a plurality of protectors and a first seal element coupled to the protectors. In a preferred embodiment, at least one of the protectors comprises a proximal bump configured to contact and shield the large instrument from contacting the first seal element which preferably comprises a radially stretchable septum.

The second seal assembly is configured to form the second seal with the large instrument. The second seal assembly comprises a guide and a second seal element coupled to the guide. The guide may comprise a funnel. The second seal element may be shaped as a cup and be mounted on a distal portion of the funnel. The first seal element may be composed of a first material that is more flexible than a second material comprising the second seal element. The second material may be more puncture-resistant than the first material.

Disposed distally of the first assembly and the second assembly, the third seal assembly comprises a third seal element. The third seal element preferably comprises a zero-seal, such as a duckbill-type seal. The third seal element defines a plenum in which at least a portion of the second seal assembly is disposed.

In a further aspect, a trocar system comprises a housing having a proximal portion and a distal portion, a cap assembly, a guide assembly coupled distally of the cap assembly and disposed at least in part within the housing, and a zero seal element. The cap assembly comprises a cap coupled to the proximal portion of the housing, a plurality of protectors, and a small-sized seal element coupled to the protectors. The guide assembly comprises a tube, and a large-sized seal mounted to a distal portion of the tube and disposed coaxially to the small-sized seal element. The zero seal element is disposed at least in part within the housing and disposed coaxially to the large-sized seal element and the small-sized seal element. The zero seal element has a distal end that is disposed adjacent to the distal portion of the housing and located distally of the small-sized seal element and the large-sized seal element. The system may further comprise a cannula formed integrally with the housing and extending distally therefrom.

A method for automatically forming a seal with instruments of varying sizes inserted through a trocar assembly is provided. The method comprises the steps of inserting an instrument through a small orifice defined by a plurality of protectors and a first seal element, inserting the instrument through a guide and a large orifice defined by a second seal element, forming a seal with the instrument with either the first seal element or second seal element, and forming a zero seal when the instrument is not inserted through the trocar assembly.

When a small instrument is being inserted, the step of forming a seal with the instrument with either the first seal element or second seal element comprises the step of forming a sealing with the small instrument with the first seal element. When a large instrument is being inserted, the step of forming a seal with the instrument with the first seal element or second seal element comprises the step of forming a seal with the large instrument with the second seal element.

In a further aspect, a trocar assembly for receiving alternatively a small instrument having a first diameter and a large instrument having a second diameter greater than the first diameter is provided. The assembly comprises a pivotal seal sized to form a first seal with the small instrument and configured to pivot upon entry of the large instrument. A hinged carrier is coupled to the pivotal seal and movable between an operable position and a released position. A releasable lock is coupled to the hinged adapter and configured to release the carrier upon engagement with the large instrument. A first floating ring is coupled to the pivotal seal and disposed in a first enclosure. A primary seal is disposed co-axially to the pivotal seal and sized to form a second seal with the large instrument. A second floating ring is coupled to the primary seal and disposed in a second enclosure. A zero seal provides a plenum to allow pivoting of the pivotal seal.

The assembly further comprises a spring biasing the adapter toward the operable position. The zero seal may comprise a duckbill-type seal. The primary seal is disposed proximally to the pivotal seal.

In a further aspect, a universal trocar system is provided for alternatively receiving a small instrument with a first diameter and a large instrument with a second diameter greater than the first diameter. The system comprises an elongate cannula and a valve housing coupled to the cannula. The valve housing forms with the cannula a working channel. A first valve is disposed in the valve housing and is sized and configured to form a first seal with the small instrument. A carrier is included in the valve housing and adapted to carry the first valve pivotally with respect to the housing between a first position wherein the first valve is disposed across the working channel, and a second position wherein the valve is displaced from the working channel. The system comprises means for releasably locking the carrier in the first position. The releasably locking means automatically releases the carrier upon contact with the large instrument to permit movement of the first valve from the first position to the second position. A second valve is disposed in the valve housing coaxially with the first valve in the first position and adapted to form a second seal with the large instrument. A zero-seal valve is disposed coaxially with and distally of the first valve and the second valve.

The system further comprises a floating ring coupled to the carrier and disposed in a radial enclosure. The system may also comprise a floating ring coupled to the second valve and disposed in a radial enclosure. The zero-seal assembly preferably comprises a duckbill-type seal element.

A method for alternatively and automatically forming a seal with a small instrument and a large instrument inserted through a trocar assembly is provided. The method comprises inserting the small instrument through a large orifice defined by a large seal, inserting the small instrument through a small orifice defined by a small pivotal seal disposed coaxially to the large seal, forming a first seal around the small instrument with the small pivotal seal, accommodating lateral movement of the small instrument with a first floating ring coupled to the small pivotal seal, inserting the large instrument through the large orifice defined by the large seal, forming a second seal around the large instrument with the large seal, automatically pivoting the small pivotal seal away with the insertion of the large instrument, and accommodating lateral movement of the large instrument with a second floating ring coupled to the large seal.

The step of automatically pivoting the small pivotal seal away with the insertion of the large instrument comprises the step of exerting an entry force with the large instrument on a hinged adapter coupled to the pivotal seal.

The method may further comprise the steps of releasably locking the small pivotal seal in an operative position and automatically releasing the small pivotal seal upon insertion of the large instrument. The method further comprises step of biasing the pivotal seal toward an operative position.

In summary, a multi-seal trocar system includes a plurality of co-axial sealing elements adapted for forming a seal with either a large or small instrument. Small and large sealing elements are disposed in an in-line arrangement such that a single port is provided for instrument insertion. A zero seal is disposed distally of the sealing elements to seal a working channel of the system and to prevent backflow when no instruments are inserted. The small sealing element is configured such that insertion of a large instrument automatically moves the small sealing element out of its path, thereby avoiding contact with the large instrument.

The invention, now having been briefly summarized, may be better understood and appreciated with a description of preferred embodiments of the concept and reference to the associated drawings.

DETAILED DESCRIPTION OF THE PREFERRED EMBODIMENTS AND BEST MODE OF THE INVENTION

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

Figure 1:
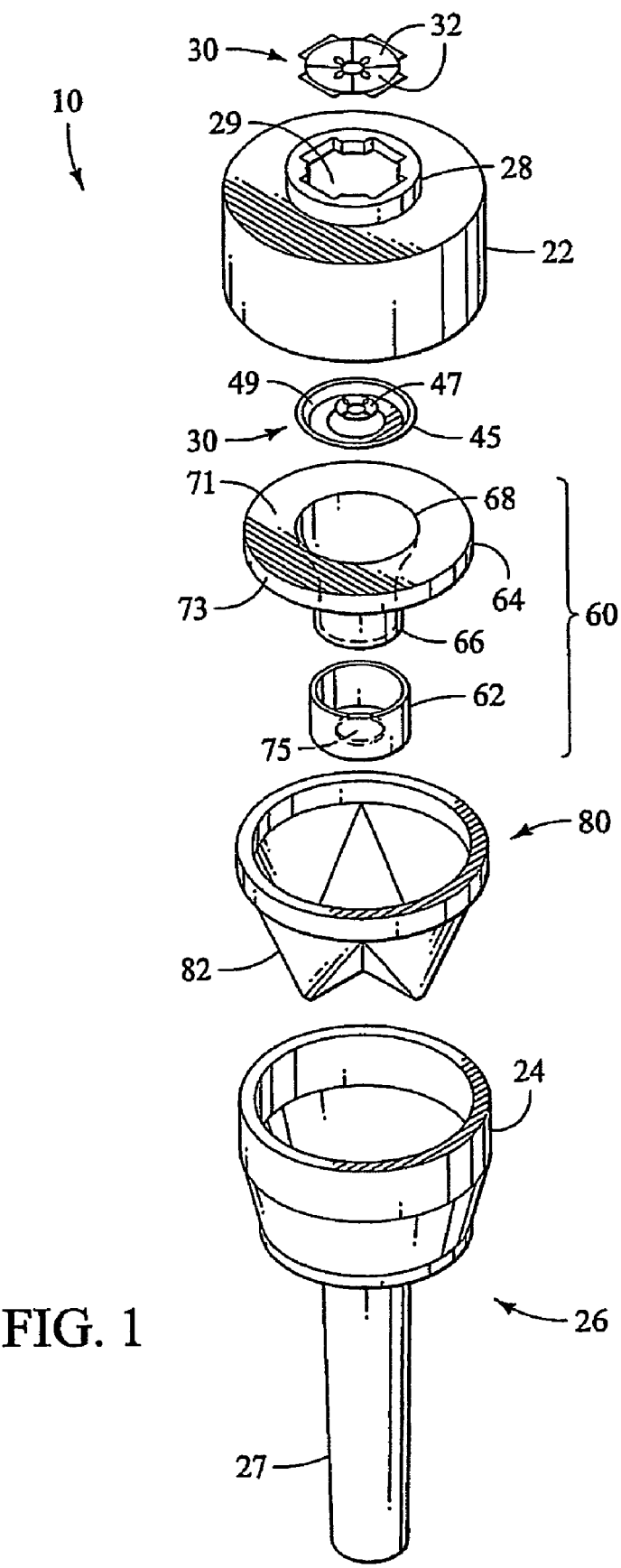
FIG. 1 is an exploded view of a first preferred trocar system according to the invention.

A first preferred embodiment of a trocar apparatus is illustrated in FIG. 1 and designated generally by the reference numeral 10. The trocar apparatus 10 comprises a seal assembly for forming a seal with large instruments, a seal assembly for forming a seal with small instruments, and a seal assembly for preventing fluid backflow when no instrument is present in the apparatus.

Figure 2:
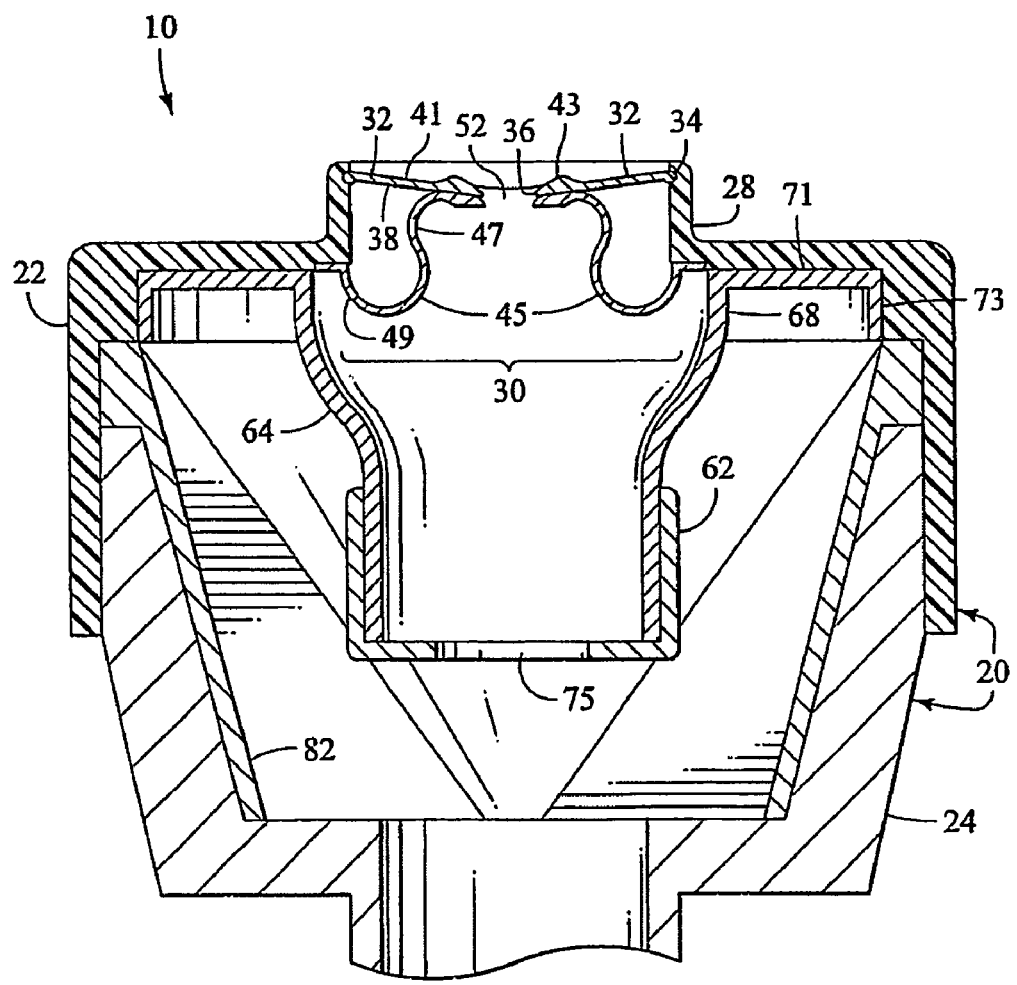
FIG. 2 is an axial cross-sectional view of the first preferred trocar system.
Figure 3:
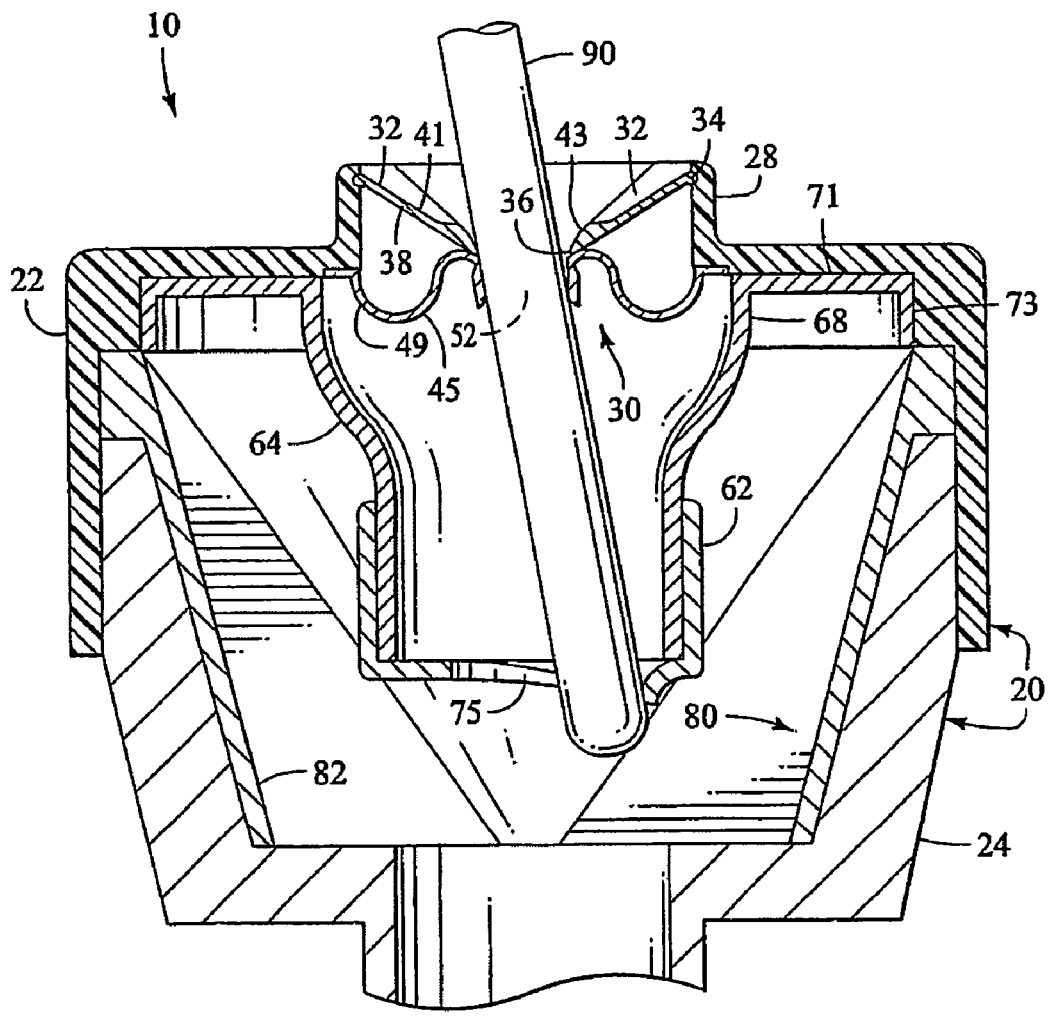
FIG. 3 is an axial cross-sectional view of the first preferred trocar system accommodating a small instrument.

In FIGS. 1-3, the apparatus 10 includes a housing 20 comprising a proximal housing portion 22 and a distal housing portion 24. In a preferred embodiment, the proximal housing portion 22 comprises a cap while the distal housing portion 24 comprises a proximal end portion of a separate cannula 26. The housing 20 defines an operative working channel in which an instrument inserted therethrough may be moved.

The cannula 26 also includes a cannula tube 27. The proximal housing portion 22 has a circular edge 28 that defines a cap orifice 29.

A first seal assembly 30 is coupled to the proximal housing portion 22 and adapted for forming a seal small instruments. As the proximal-most seal assembly of the apparatus 10, the first seal assembly 30 comprises a plurality of protectors 32 disposed in the cap orifice 29. In the preferred embodiment, the protectors 32 comprise hinged levers, or leaves, coupled to the proximal housing portion 22. More specifically, an outer end portion 34 of each protector 32 is hinged to the circular edge 28 of the proximal housing portion 22. Each protector 32 extends radially inward from the outer end portion 34 to an inner end portion 36. In the rest state or detente position, each protector 32 has a distally facing side 38 and a proximally facing side 41. The inner end portion 36 of each protector 32 includes a bump, or projection 43, on the proximally facing side 41.

The first seal assembly 30 includes a small seal element, or small sealing valve 45, configured to seal small instruments. The small sealing valve 45 preferably comprises an elastomeric septum shaped as a saucer with a proximally extending central portion 47 and an outer portion 49. The central portion 47 of the small sealing valve 45 is preferably coupled to the distally facing sides 38 of the protectors 32 while the outer portion 49 is coupled to the proximal housing portion 22 adjacent to the circular edge 28. The small sealing valve 45 is radially stretchable upon rotation or flexation of the protectors 32. Thus, the protectors 32 and the small sealing valve 45 collectively define a variable orifice 52 that is expandable from a small diameter to a large diameter as will be described further below.

In an alternative embodiment (not shown), the small sealing valve 45 need not be coupled to the protectors 32. In such an embodiment, the end portions 36 of the protectors 32 may rotate outwardly and distally into the orifice of the septum, thereby stretching the septum and predilating, or enlarging, the orifice.

The apparatus 10 includes a second seal assembly 60 adapted for forming a seal with large instruments. The second seal assembly 60 comprises a large sealing valve 62 disposed distally and coaxially to the small sealing valve 45. The large sealing valve 62 is configured to seal large instruments. The second seal assembly 60 includes a tube, or funnel 64, that is tapered distally such that a distal diameter at a distal funnel portion 66 is smaller than a proximal diameter at a proximal funnel portion 68. The funnel 64 includes an annular flange 71 and a rim 73 that are coupled to the proximal housing portion 22. The funnel 64 is axially aligned with the cannula tube 27 and the first seal assembly 30.

In a preferred embodiment, the large sealing valve 62 comprises a cup shaped seal mounted to the tapered distal funnel portion 66. The large sealing valve defines a large orifice 75.

The apparatus 10 also includes a third seal assembly 80 configured to prevent fluid backflow when no instrument is present. The third seal assembly 80 comprises a zero seal element 82 sized and configured to perform as a shut-off valve. The zero seal element 82 is coupled to a distal and interior side 84 of the distal housing portion 24. In the preferred embodiment, the zero seal element 82 comprises a duckbill-type seal, such as a single or double duckbill seal. The zero seal element 82 provides sufficient room for accommodating a majority of the funnel 64 and the large sealing valve 62.

FIG. 3 is an operative view of the apparatus 10 accommodating a small instrument 90. As the small instrument 90 is inserted through the first seal assembly 30, it encounters the protectors 32 and the small sealing valve 45. The protectors 32 pivot distally and guide the small instrument 90 toward the large sealing valve 62. In prior art trocars, insertion of a small instrument typically imposes a "side-load" on the seal, thereby elongating the orifice. In the preferred embodiment, elongation of the orifice is eliminated, or at least minimized, by limiting any side-to-side motion of the small instrument 90.

Figure 4:
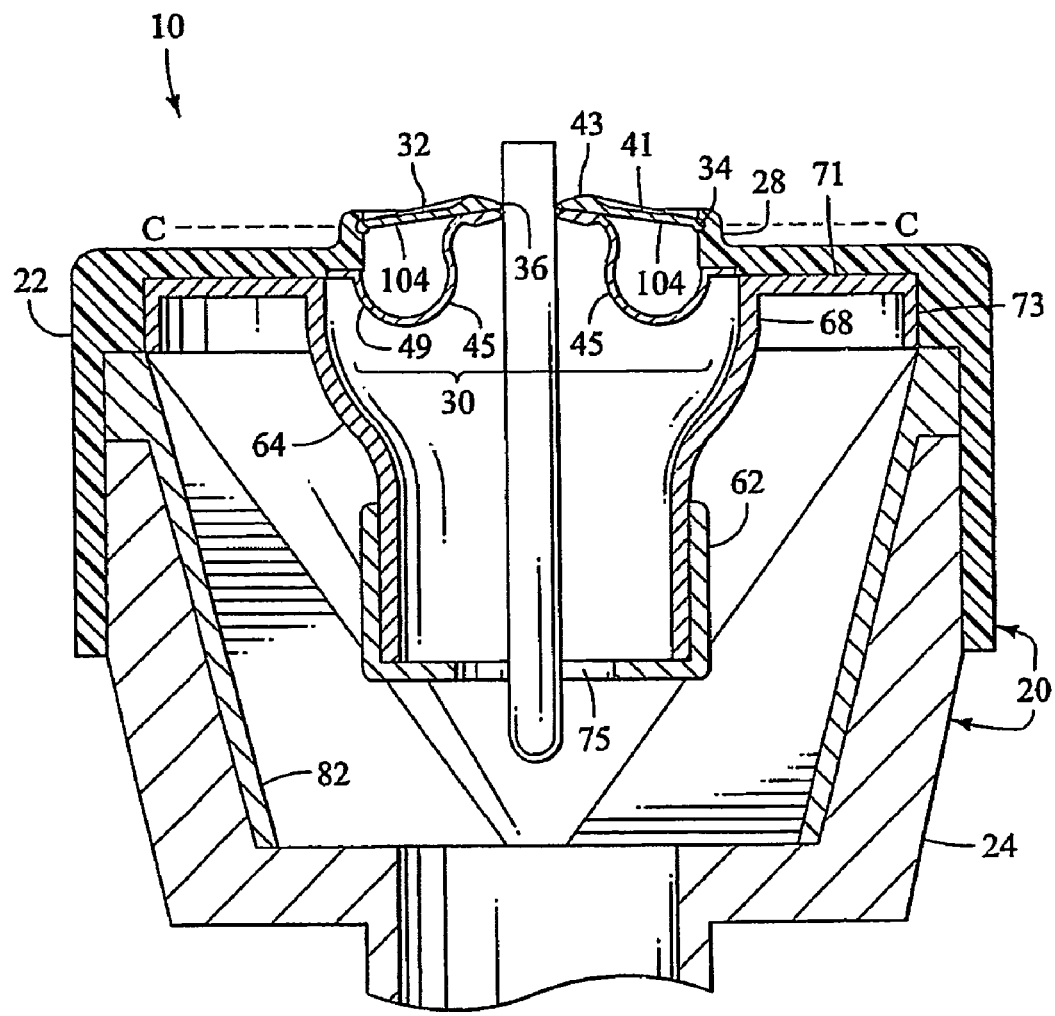
FIG. 4 is an axial cross-sectional view of the first preferred trocar system accommodating the small instrument with protectors proximally angled.
Figure 5:
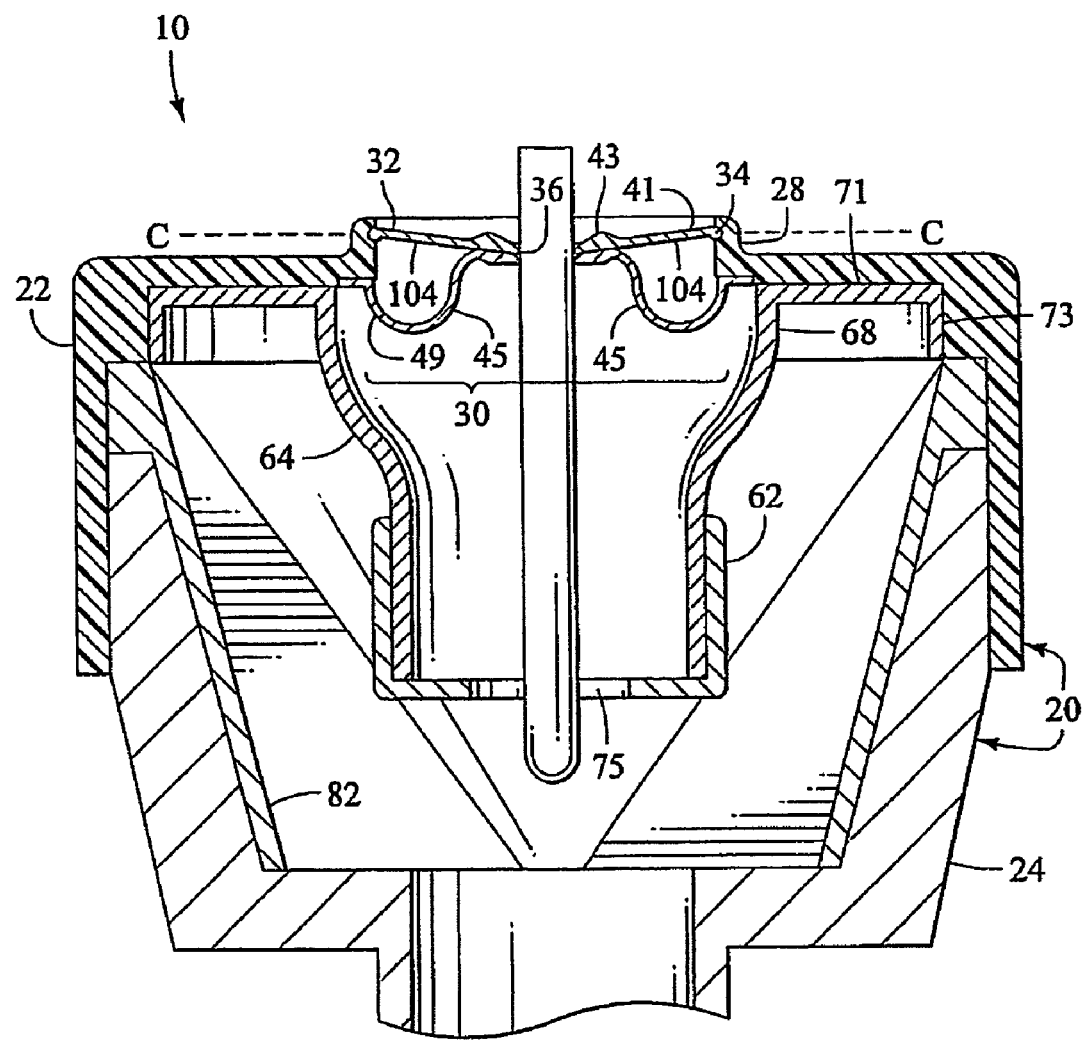
FIG. 5 is an axial cross-sectional view of the first preferred trocar system accommodating the small instrument with protectors distally angled.

This is accomplished by angling the protectors 32 in relation to the proximal housing portion 22 such that rotation of the protectors 32 is dependent upon forward, or distal, motion of the instrument 90. Any side load would not carry enough leverage to rotate the protectors 32 past their "over-center" or "détente" (at-rest) position. As examples and not by way of limitations, the angles may range from $-5°$ with respect to a horizontal plane "C" such that the protectors 32 are angled proximally in an "over-center" configuration to $+45°$ wherein the protectors 32 are angled distally. FIG. 4 illustrates an example of an over-center, détente configuration wherein the protectors 32 are negatively angled. FIG. 5 illustrates a positively angled position of the protectors 32. Upon further insertion, the small instrument 90 extends through the large orifice 75 defined by the large sealing valve 62 and ultimately through the third seal assembly 80.

Figure 6:
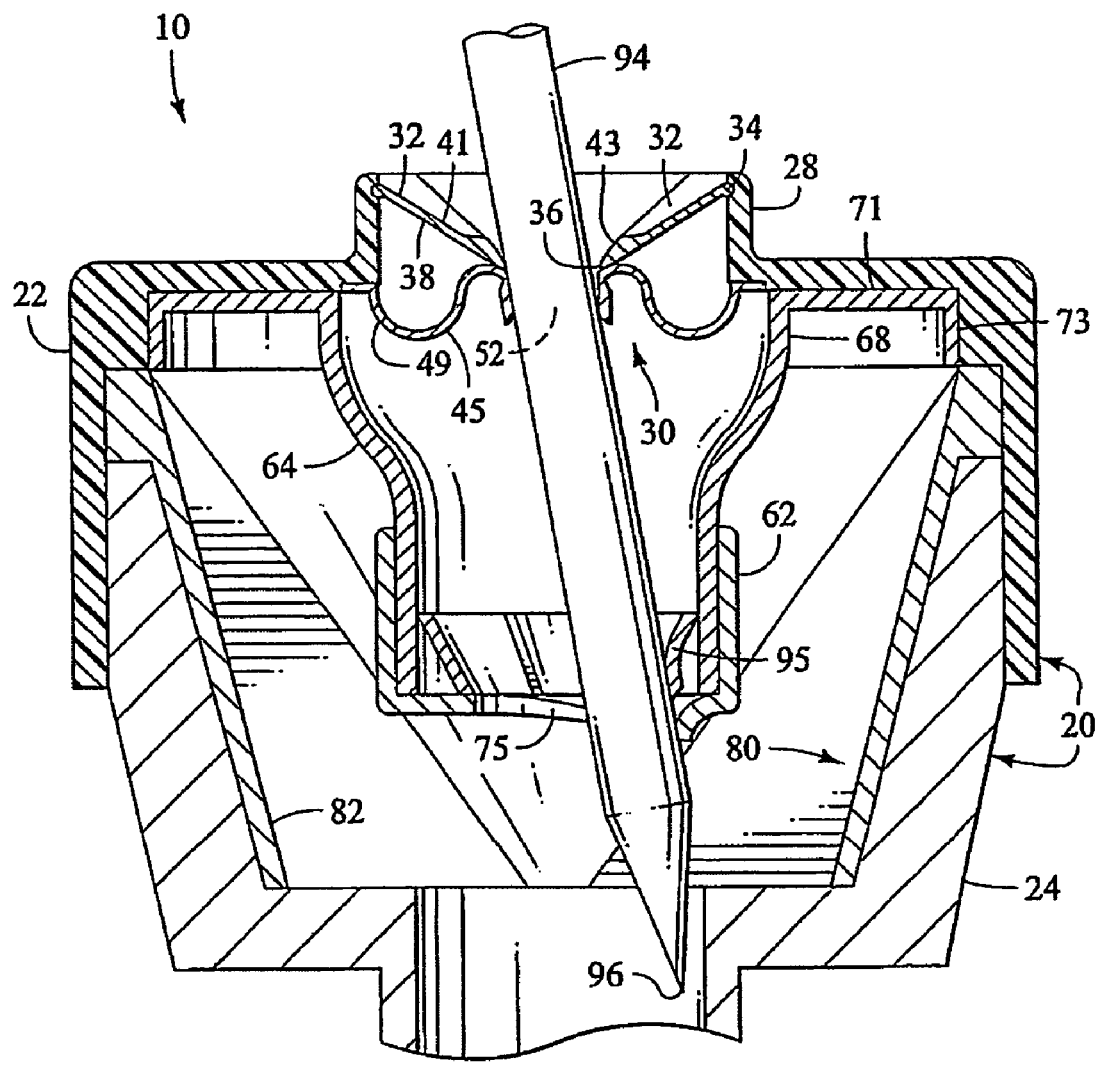
FIG. 6 is an axial cross-sectional view of the first preferred trocar system accommodating a small, pointy instrument.

In FIG. 6, it will be appreciated that the apparatus 10 also accommodates a small instrument 94 with a sharp distal tip 96. By placing the large sealing valve 62 distant from the variable orifice 52, the small instrument 94 is guided into a preferred position where it does not pose an inordinate threat to the large sealing valve 62. Furthermore, a series of flaps or leaves 95 may be optionally provided to direct small instruments toward the large orifice, thereby minimizing damage to the large sealing valve 62.

Figure 7:
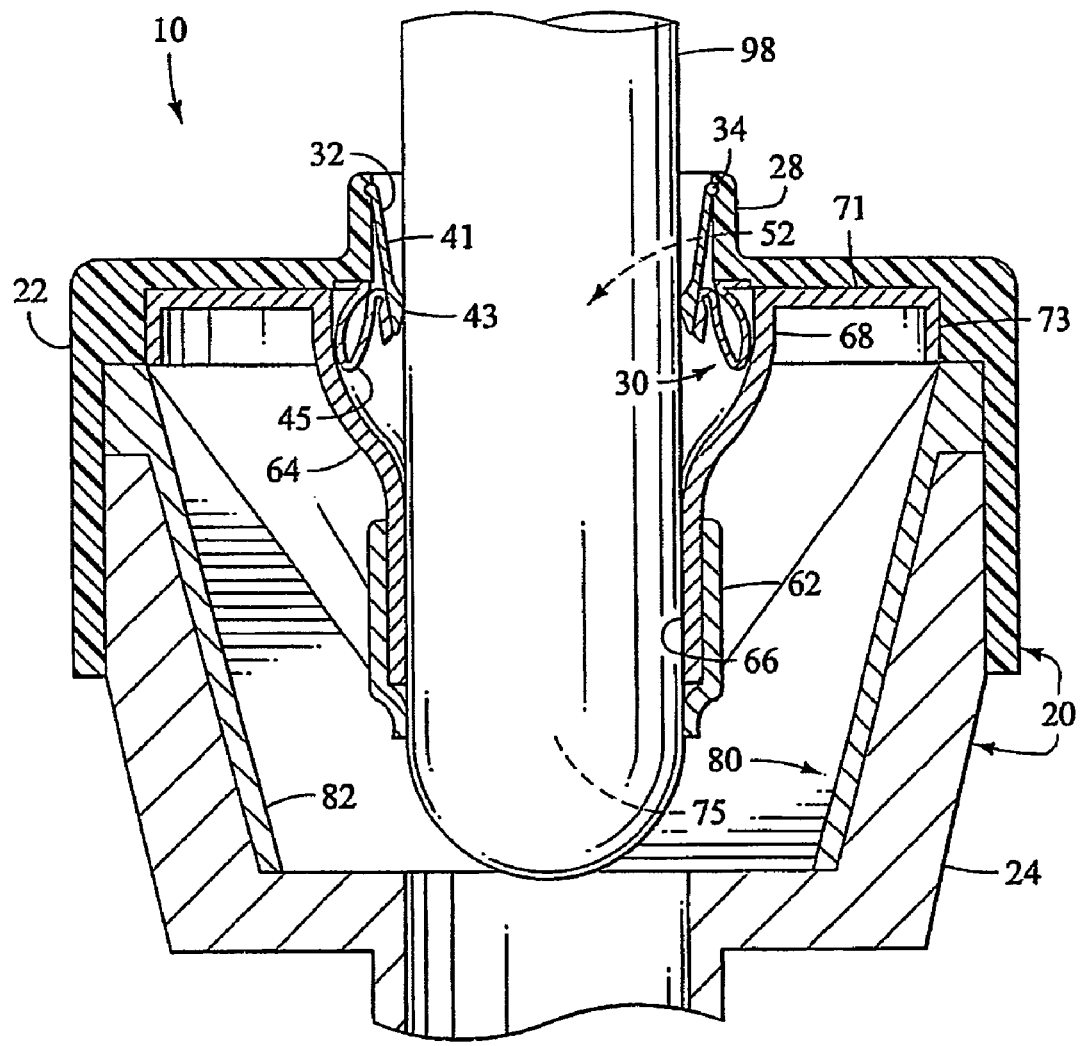
FIG. 7 is an axial cross-sectional view of the first preferred trocar system accommodating a large instrument.

FIG. 7 is an operative view of the apparatus 10 accommodating a large instrument 98. As the large instrument 98 is inserted through the first seal assembly 30, the instrument 98 contacts the proximally facing side 41 of the protectors 32 and causes the protectors 32 to rotate upon their hinges 36 so that the associated variable orifice 52 is stretched to a diameter larger than that of the large instrument 98. This enlargement of the orifice 52 and predilation of the small sealing valve 45 is accomplished in part by the raised bumps 43. The bumps 43 facilitate exaggerated rotation of the protectors 32, and, thus, stretching of the small sealing valve 45 which is carried by the protectors 32.

It will be appreciated that the small sealing valve 45 is stretched radially beyond the range of contact with the inserted large instrument 98, thereby avoiding any damage which may be caused by contact with the large instrument. Therefore, the small sealing valve 45 may be composed of a more delicate and flexible material that would otherwise be too delicate or subject to puncture, tearing or wear as a result of contact. Such a material may comprise, for example, silicone rubber, polyisoprene, vinyl, polyurethane elastomers, or C-Flex®, a trademark of CONSOLIDATED POLYMER TECHNOLOGIES, INC. Such a material may also comprise a combination of components, including styrene-ethylene-butylene-styrene (SEBS) block co-polymers, polyolefins, mineral oils and silicone oils.

Other advantages of overstretching include a smoother insertion since the septum material of the small sealing valve 45 does not present a frictional drag on the large instrument 98. Instead, the large instrument 98 glides over the protectors 32 which may be composed of a rigid, lubricious material. The shape and choice of material of the bumps 43 will solely determine the friction of the first seal assembly on a large instrument. Any high coefficient of friction which might typically be associated with the small sealing valve 45 will not affect the large instrument.

As the large instrument 98 is further inserted, it is guided by the funnel 64 toward the large sealing valve 62 which seals the large instrument 98. The need to control any side-to-side motion of the large instrument 98 is eliminated by placing the large sealing valve 62 deep within the housing 20, for example, distant from the proximal housing portion 22, and adjacent to the distal end portion 66 of the funnel 64. In this position, the large instrument 98 does not have room to elongate or deform the large orifice 75 because the funnel 64 restricts any side-to-side motion. Thus, the large orifice 75 need only provide marginal engagement with the large instrument 98 since the instrument 98 is forced to remain within the confines of the funnel 64.

Since the large orifice 75 need not be stretched or dilated, the large sealing valve 62 may be composed of a more durable and puncture resistant material than that of the small sealing valve 45. For example, and not by way of limitation, the large sealing valve 62 may be composed of natural latex rubber, polyisoprene, or a fabric reinforced elastomeric material.

Figure 8:
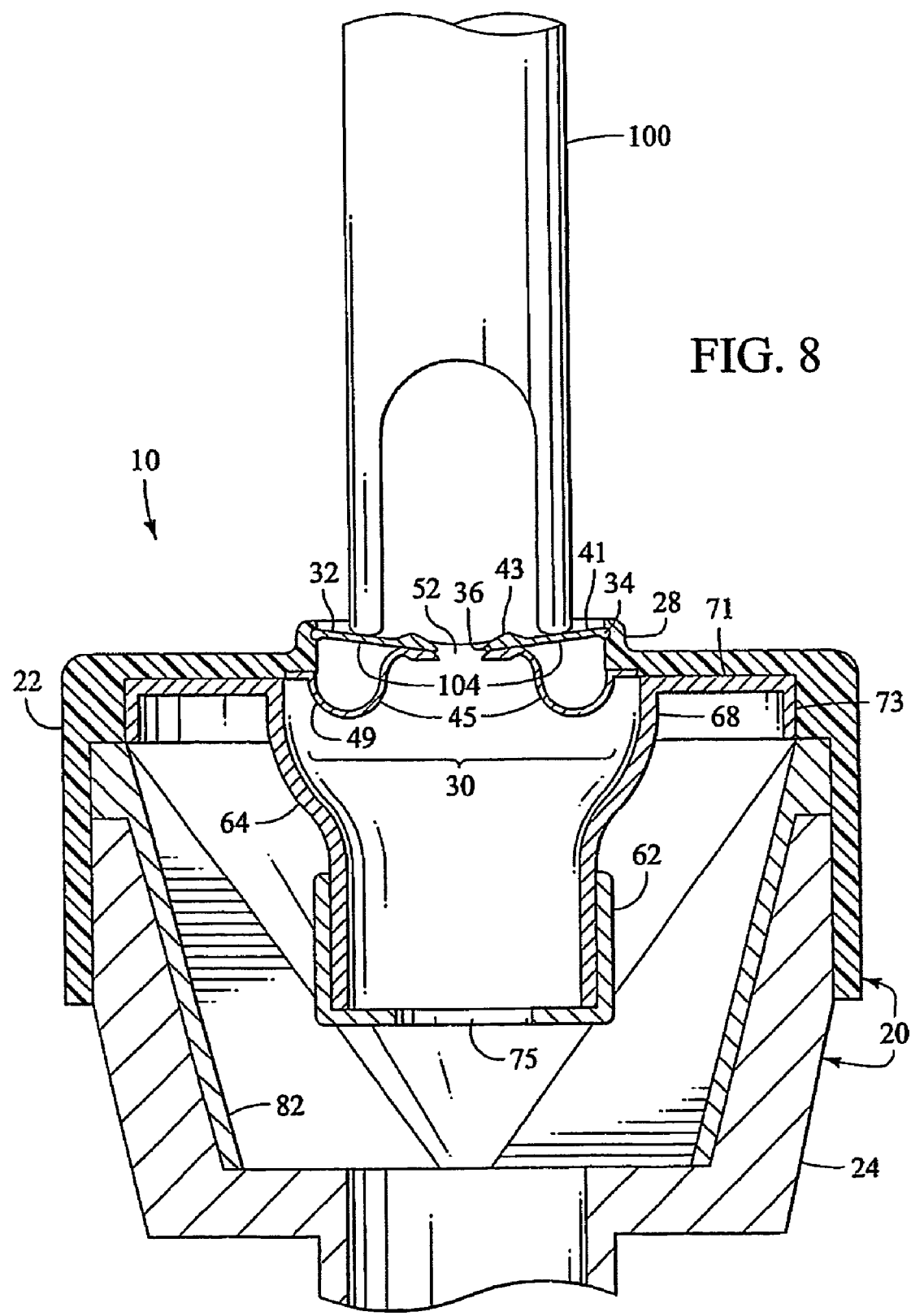
FIG. 8 is an axial cross-sectional view of the first preferred trocar system initially accommodating a large, pronged instrument.
Figure 9:
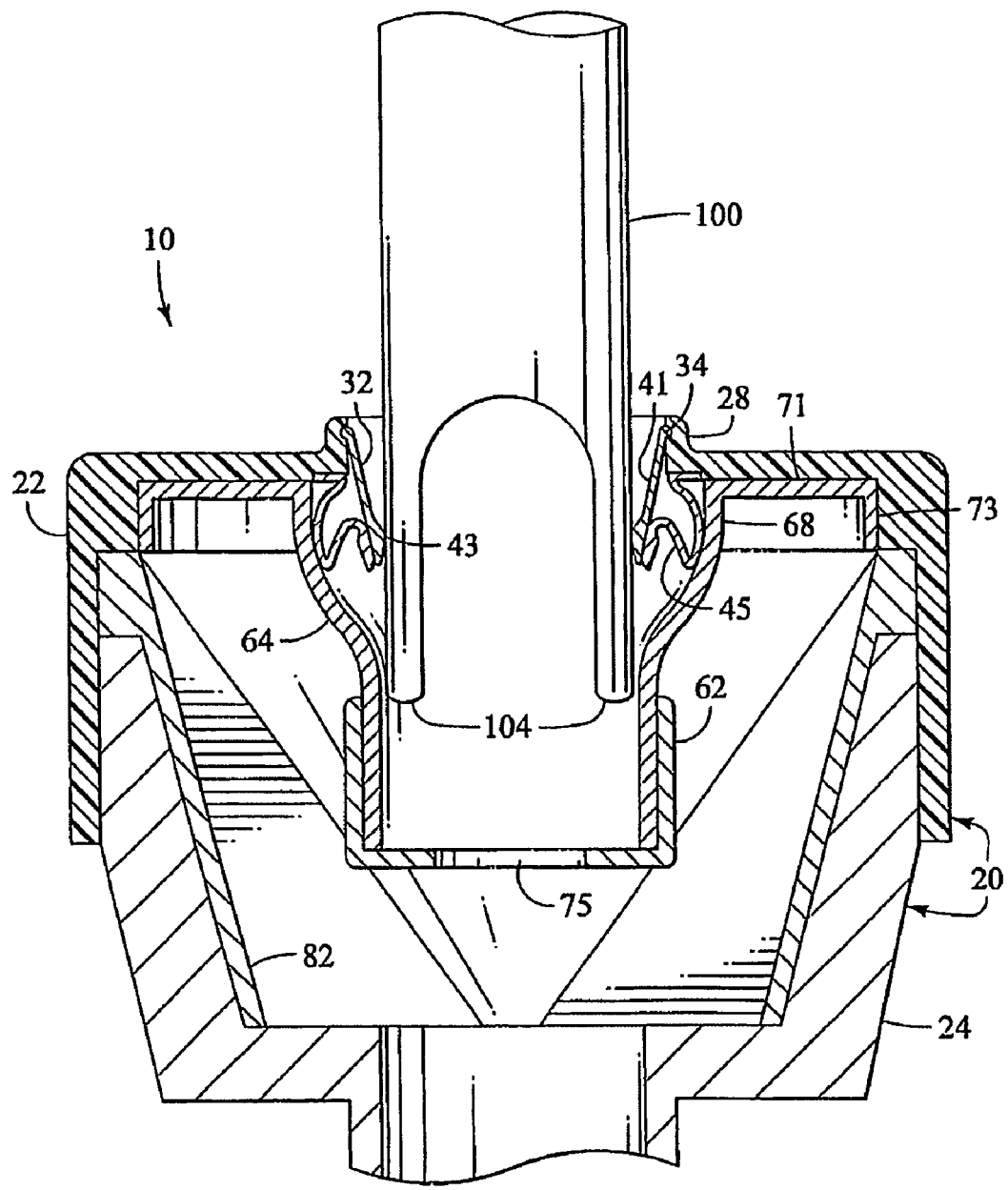
FIG. 9 is an axial cross-sectional view of the first preferred trocar system subsequently accommodating the large, pronged instrument.
Figure 10:
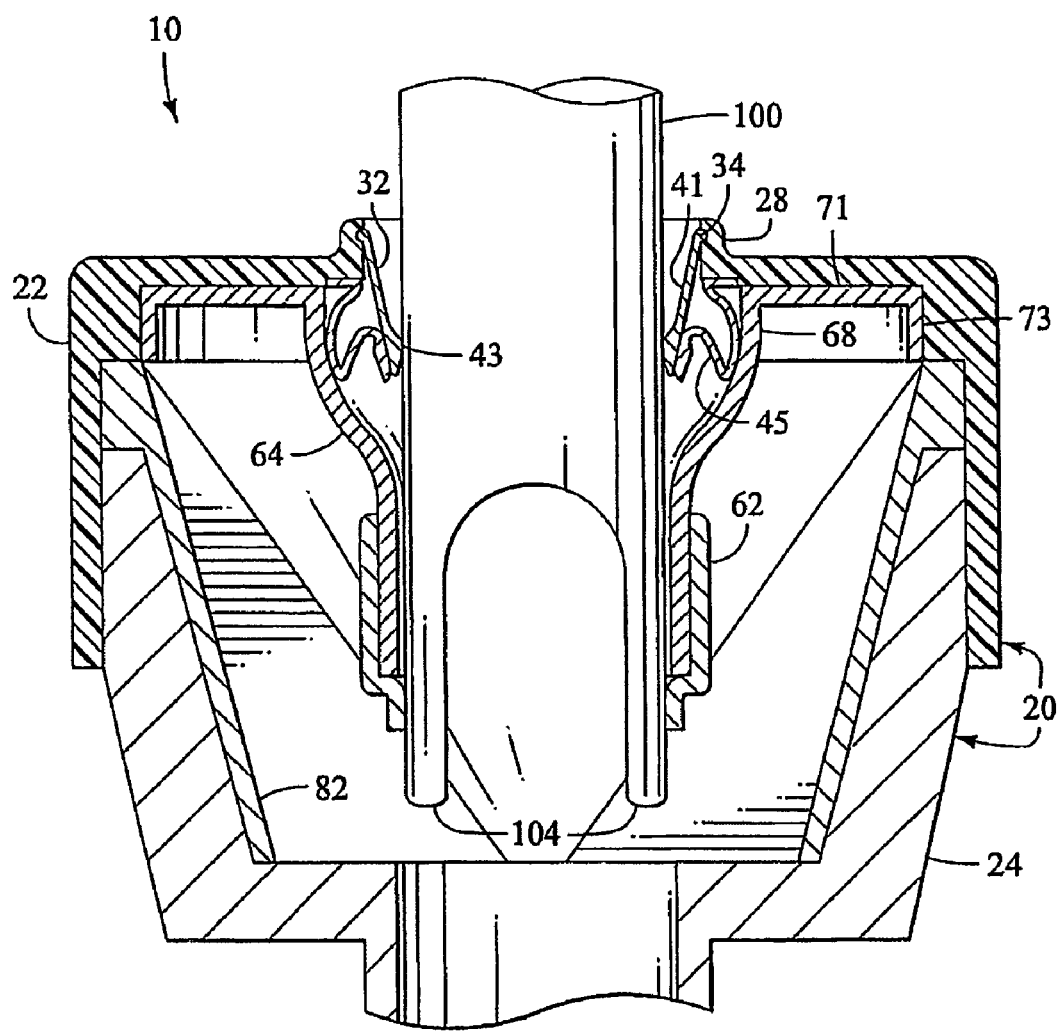
FIG. 10 is an axial cross-sectional view of the first preferred trocar system ultimately accommodating the large, pronged instrument.

FIGS. 8-10 illustrate the apparatus 10 progressively accommodating an alternate large instrument 100 having a pronged distal portion 102 with tips 104. As the large instrument 100 is inserted, the tips 104 initially contact the proximally facing side 41 of the protectors 32. Upon further entry, the tips 104 glide over the bumps 43 as the protectors 32 pivot distally, thereby shielding the small sealing valve 45 from any contact with the large instrument 100. The large sealing valve 62 and the zero seal element 82 automatically seal the large instrument 100 as it is further inserted.

Figure 11:
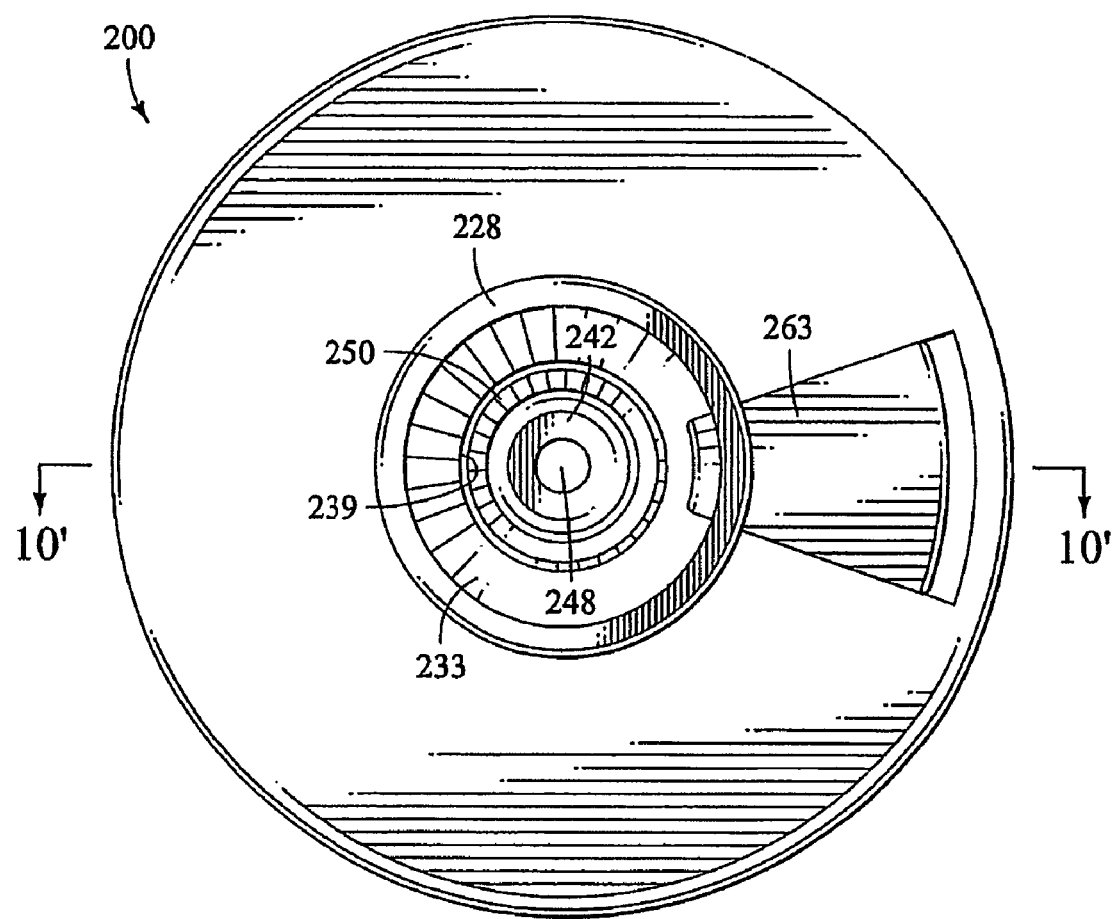
FIG. 11 is a top plan view of a second preferred trocar system according to the invention.
Figure 12:
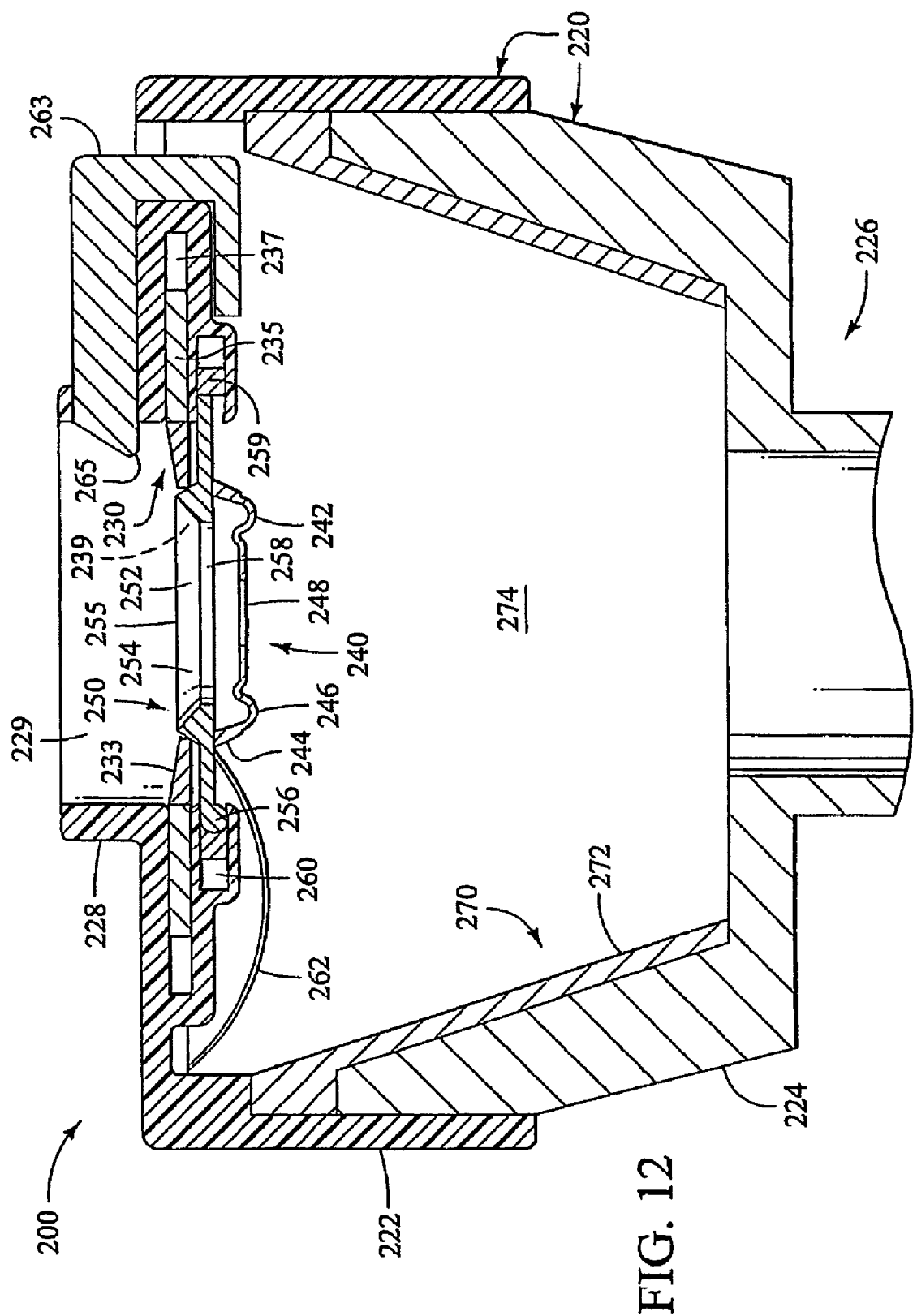
FIG. 12 an axial cross-sectional view of the second preferred trocar system.

A second preferred embodiment of a trocar system illustrated in FIGS. 11-14 includes a self-adjusting apparatus designated generally by the reference numeral 200. In FIGS. 11 and 12, this self-adjusting apparatus 200 includes a housing 220. The housing 220 comprises a first, proximal housing portion 222 coupled to a second, distal housing portion 224. In the preferred embodiment, the proximal housing portion 222 comprises a cap while the distal housing portion 224 comprises a proximal end portion of a separate cannula 226. Thus, the two housing portions 222, 224 collectively form the housing 220. The proximal housing portion 222 includes a tube 228 that defines a port 229 and leads to the following seal assemblies. The housing 220 defines an operative working channel in which an inserted instrument may be moved.

The apparatus 200 comprises a first, primary seal assembly 230 adapted for forming a seal with large instruments. This primary seal assembly 230 comprises a relatively large seal element, or large sealing valve 233, coupled radially and inwardly to a floating ring 235. The floating ring 235 is disposed within a radial enclosure 237 defined by the proximal housing portion 222. The enclosure 237 that provides sufficient space for the large seal assembly 230 to move laterally, namely, side-to-side. The large sealing valve 233 defines a large orifice 239.

In FIG. 12, the apparatus 200 further comprises a second, pivotal seal assembly 240 adapted for forming a seal with small instruments. In the preferred embodiment, this pivotal seal assembly 240 is disposed distally and axially to the large seal assembly 230. The pivotal seal assembly 240 includes a relatively small seal element, or small sealing valve 242, that preferably comprises an elastomeric structure having an outside wall 244 and a convoluted inner portion 246 that defines a small orifice 248. The small seal element 242 is made pivotal by being coupled to an internal, pivotal carrier, or adapter 250. The small, pivotal sealing valve 242 is disposed axially to the large sealing valve 233.

The pivotal adapter 250 comprises a generally annular structure having a raised bumper, or guide 252. In the preferred embodiment, the bumper 252 is disposed at least in part within the large orifice 239. The bumper 252 includes a slanted surface 254 that extends distally and centrally from a raised annular tip 255. The bumper 252 serves both as a guide for directing small instruments to the small sealing valve 242, and as a bumper for engaging large instruments. The pivotal adapter 250 is preferably hinged at a point 256 beneath the first radial enclosure 237. The pivotal adapter 250 defines an adapter orifice 258 positioned in between the large orifice 239 and the small orifice 248.

The pivotal seal assembly 240 floats by virtue of the adapter 250 being coupled to a second floating ring 259 disposed within a second enclosure 260. In particular, the adapter 250 is hinged to the second floating ring 259.

A spring mechanism 262 coupled to the proximal housing portion 222 biases the pivotal adapter 250, and thus the pivotal seal assembly 40, toward an operative position shown in FIG. 12. The spring mechanism 260 preferably comprises a bow spring, although a variety of other springs may be employed.

A latch 263 coupled to the proximal housing portion 222 releasably holds the pivotal seal assembly 240 in the operative position. The latch 263 includes a projection 265 configured to contact large instruments. As will be described later, contact of the projection 265 by a large instrument activates the latch 263 which then releases the pivotal seal assembly 240.

The apparatus 200 further comprises a third seal assembly 270 adapted to perform both as a shut-off valve and as an additional seal upon the instrument inserted therethrough. In a preferred embodiment, the third seal assembly 270 comprises a zero seal element 272 coupled to an inner surface 274 of the distal housing portion 224. The zero seal element 272 functions as a shut-off valve by providing a seal against fluid backflow when no instruments are inserted therethrough. The zero seal element 272 comprises a duckbill-type seal such as a single duckbill seal or a double duckbill seal. The zero seal element 272 is thus disposed in a cavity 274 defined by housing 220. As will be shown below, the zero seal element 272 is large enough to provide sufficient room for the pivotal seal assembly 240 to swing.

Figure 13:
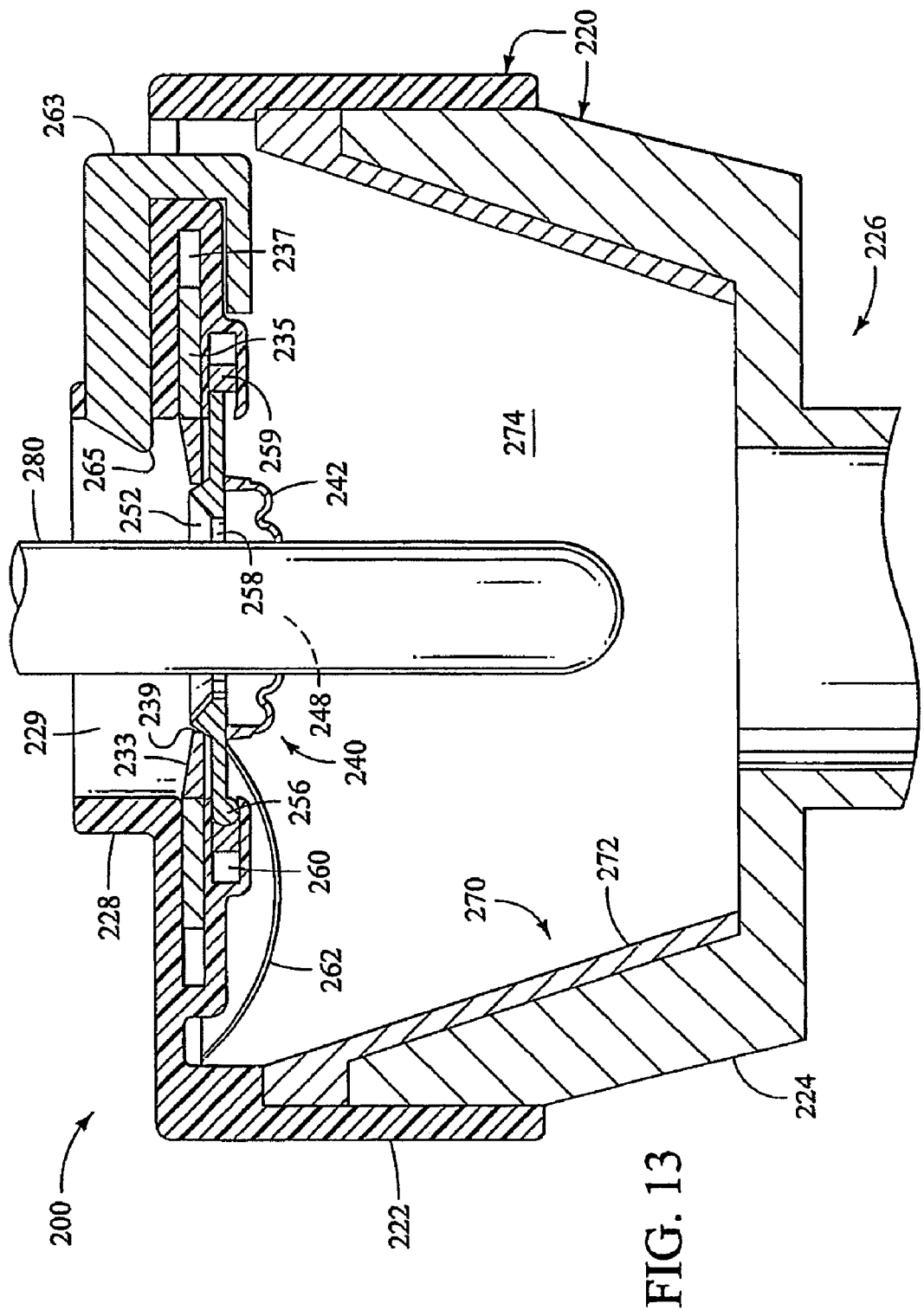
FIG. 13 is an axial cross-sectional view of the second preferred trocar system accommodating a small instrument.

FIG. 13 is an operative view of the self-adjusting trocar apparatus 200 accommodating a small instrument 280. When inserted, the small instrument 280 extends through the large orifice 239 primarily untouched by the large sealing valve 233. The bumper 252 helps guide the small instrument 280 through its adapter orifice 258 toward the small orifice 248 defined by the small sealing valve 242. The small sealing valve 242 effectively forms a seal with the small instrument 280.

It will be appreciated that since the small sealing valve 242 need not be dilated, it may be composed of a less compliant material than those feasible with prior art trocars. A more rigid material comprising the small sealing valve 242 would also provide a more effective seal against the small instrument 280. As the small instrument 280 is further inserted through the third seal assembly 270, the zero seal element 272 provides an additional, secondary seal against the small instrument 280. The small sealing assembly 240 accommodates any lateral movement of the small instrument 280 by virtue of its floating characteristics provided by the second floating ring 259

Figure 14:
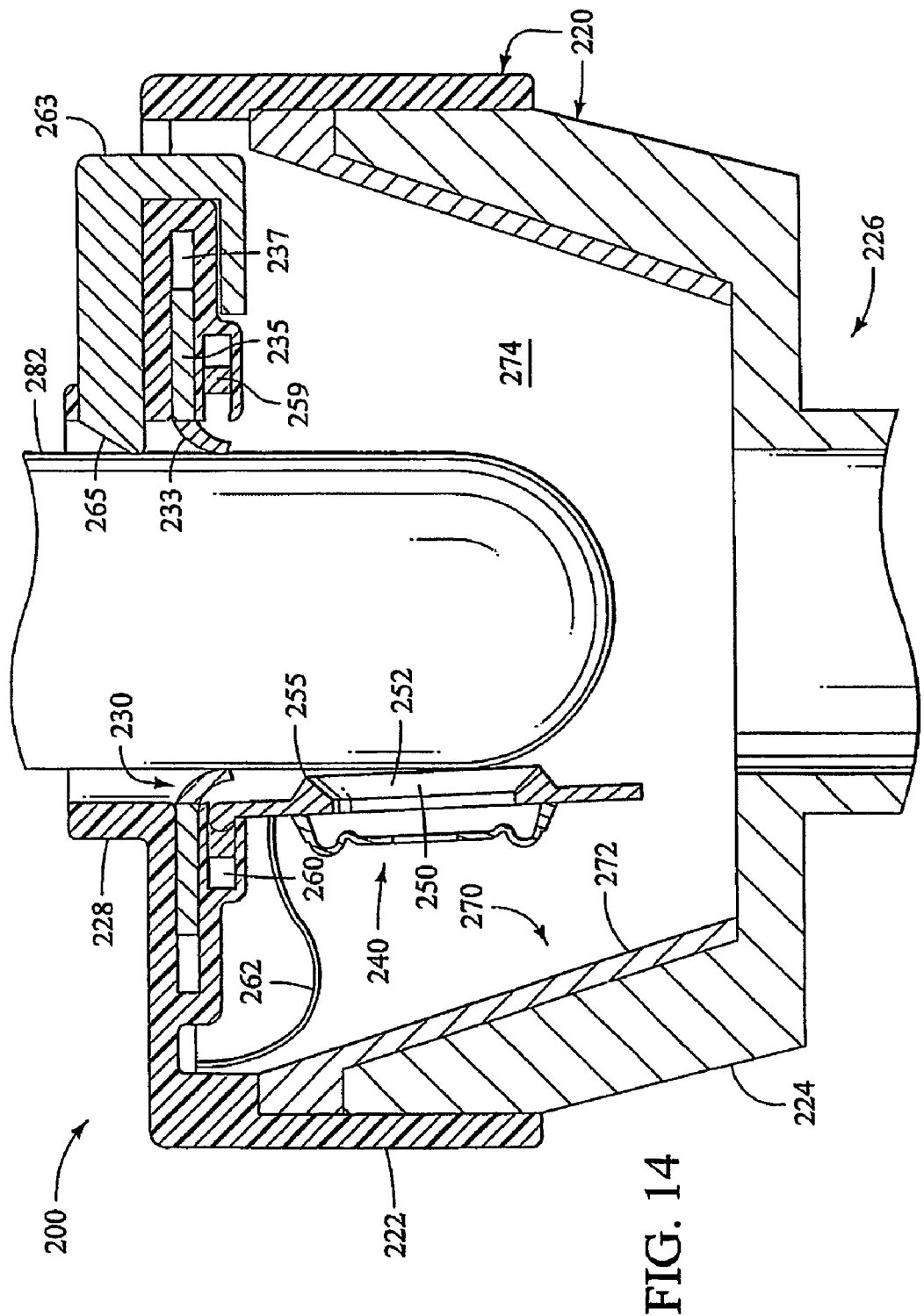
FIG. 14 is an axial cross-sectional view of the second preferred trocar system accommodating a large instrument.

The self-adjusting feature of the trocar apparatus 200 is illustrated in FIG. 14. As a large instrument 282 is inserted into the proximal tube 228, the large instrument 282 contacts the projection 265, thus activating the latch 263 which releases the pivotal seal assembly 240, Once released, the pivotal seal assembly 240 does not automatically swing away since the spring mechanism 260 still biases the pivotal seal assembly 240 toward the operative position. The pivotal seal assembly 240 is, however, unlocked and, therefore, permitted to swing away.

Upon insertion through the large orifice 239, the large instrument 282 forms a seal with the sealing valve 233. When further inserted, the large instrument 282 contacts the bumper 252, and more specifically the annular tip 255, of the pivotal adapter 250. Since the pivotal seal assembly 240 is now unlocked, the distally directed entry force applied to the large instrument 282 causes the pivotal seal assembly 240 to pivot away, thereby displacing the small sealing valve 242 from the working channel. Since the pivotal assembly 240 is disposed distally of the primary seal assembly 230, the pivotal seal assembly 240 swings distally away from the primary seal assembly 230. It will be appreciated that the zero seal element 272 is large enough to provide sufficient space for the pivotal seal assembly 240 to pivot.

It will also be appreciated that though the large sealing valve 233 is preferably composed of an elastomeric material, such elastomeric material may be relatively rigid, or relatively less compliant, since the large sealing valve 233 need not accommodate lateral motion of the large instrument 282. Instead, the rigid, large sealing valve 233 may "float" with the lateral movement of the large instrument 282 as enabled by the floating ring 235. The radial enclosure 237 provides sufficient room for the floating ring 235 to move side-to-side.

In the above preferred embodiments, it will be noted that the seal assemblies therein are axially aligned such that their respective sealing valves are disposed in a coaxial relationship. Moreover, the sealing characteristics of the trocar apparatuses according to the invention are automatic. To effectuate sealing, no manual adjustment or manipulation is required of the operator other than the mere insertion of the instrument. This automatic feature will be appreciated by operators who usually do not have a free hand, or even a free finger, available for adjustment. Though multiple seals are provided for accommodating differently sized instruments, it will further be appreciated that only a single port is provided for the insertion of an instrument.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

What is claimed is:

1. A trocar assembly for receiving alternatively a small instrument having a first diameter and a large instrument having a second diameter greater than the first diameter, the assembly comprising:
    a pivotal seal sized to form a first seal with the small instrument and configured to pivot upon entry of the large instrument;
    a hinged carrier coupled to the pivotal seal and movable between an operable position and a released position;
    a releasable lock coupled to the hinged carrier and configured to release the carrier upon engagement with the large instrument;
    a first floating ring coupled to the pivotal seal and disposed in a first enclosure;
    a primary seal disposed co-axially to the pivotal seal and sized to form a second seal with the large instrument;
    a second floating ring coupled to the primary seal and disposed in a second enclosure; and
    a zero seal providing a plenum to allow pivoting of the pivotal seal.

2. The assembly of claim 1, further comprising:
    a spring biasing the carrier toward the operable position.

3. The assembly of claim 1, wherein the zero seal comprises a duckbill type seal.

4. The assembly of claim 1, wherein the primary seal is disposed proximally to the pivotal seal.

5. A universal trocar system for alternatively receiving a small instrument with a first diameter and a large instrument with a second diameter greater than the first diameter, the system comprising:
    an elongate cannula;
    a valve housing coupled to the cannula and forming with the cannula a working channel;
    a first valve disposed in the valve housing and being sized and configured to form a first seal with the small instrument;
    a carrier included in the valve housing and adapted to carry the first valve pivotally with respect to the housing between a first position wherein the first valve is disposed across the working channel, and a second position wherein the valve is displaced from the working channel;

means for releasably locking the carrier in the first position, the releasably locking means automatically releasing the carrier upon contact with the large instrument to permit movement of the first valve from the first position to the second position;

a second valve disposed in the valve housing coaxially with the first valve in the first position and adapted to form a second seal with the large instrument; and a zero-seal valve disposed coaxially with and distally of the first valve and the second valve.

6. The system of claim 5, further comprising:
a floating ring coupled to the carrier and disposed in a radial enclosure.

7. The system of claim 5, further comprising:
a floating ring coupled to the second valve and disposed in a radial enclosure.

8. The system of claim 5, wherein the zero-seal assembly comprises a duckbill-type seal element.

* * * * *